US008822443B2

(12) United States Patent
Ishihara et al.

(10) Patent No.: US 8,822,443 B2
(45) Date of Patent: Sep. 2, 2014

(54) SOLID HERBICIDAL COMPOSITION

(75) Inventors: Yoshiaki Ishihara, Kusatsu (JP); Kazutaka Ikeda, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 12/278,984

(22) PCT Filed: Jan. 15, 2007

(86) PCT No.: PCT/JP2007/050846
§ 371 (c)(1), (2), (4) Date: Aug. 11, 2008

(87) PCT Pub. No.: WO2007/105377
PCT Pub. Date: Sep. 20, 2007

(65) Prior Publication Data

US 2009/0069346 A1 Mar. 12, 2009

(30) Foreign Application Priority Data

Mar. 2, 2006 (JP) ................................ 2006-056296

(51) Int. Cl.
*A01N 43/00* (2006.01)
*A61K 31/33* (2006.01)
*A01N 47/36* (2006.01)

(52) U.S. Cl.
CPC ..................................... *A01N 47/36* (2013.01)
USPC .......................................... 514/183; 514/256

(58) Field of Classification Search
None
See application file for complete search history.

(56) References Cited

U.S. PATENT DOCUMENTS

| | | | | |
|---|---|---|---|---|
| 5,723,141 | A * | 3/1998 | Kimura et al. | 424/408 |
| 6,723,682 | B2 * | 4/2004 | Yamada et al. | 504/132 |
| 2003/0100449 | A1 | 5/2003 | Maeda et al. | |
| 2004/0023803 | A1 | 2/2004 | Jaeger et al. | |

FOREIGN PATENT DOCUMENTS

| | | | |
|---|---|---|---|
| EP | 462585 | A1 * | 12/1991 |
| EP | 0 764 404 | | 3/1997 |
| JP | 5-271021 | | 10/1993 |
| JP | 6-219913 | | 8/1994 |
| JP | 9-143015 | | 6/1997 |
| JP | 10 109903 | | 4/1998 |
| JP | 10-109903 | | 4/1998 |
| JP | 10 324606 | | 12/1998 |
| JP | 10-324606 | | 12/1998 |
| JP | 11-130607 | | 5/1999 |
| JP | 2002-12509 | | 1/2002 |
| WO | WO 2005009132 | A1 * | 2/2005 |
| WO | WO 2005/092104 | A1 | 10/2005 |

OTHER PUBLICATIONS

Guery Bernard, six new molecules for six different programs, Phytoma (1998), 511, 35-38.*

Da Silva A. et al., "Sugarcane tolerance to Flazasulfuron in isolated and sequential applications and in a mixture with other herbicides, and its effects for controlling *Cyperus rotundus* L. and other species of weeds", vol. 43, p. 102-111, XP002468363, (1996).

Office Action issued Jan. 10, 2012 in Japanese Patent Application No. 2007-004122 (with English translation).

* cited by examiner

*Primary Examiner* — Wu-Cheng Winston Shen
*Assistant Examiner* — Jean Cornet
(74) *Attorney, Agent, or Firm* — Oblon, Spivak, McClelland, Maier & Neustadt, L.L.P.

(57) ABSTRACT

To provide a solid herbicidal composition in which decomposition of the herbicidal active ingredient is suppressed, and favorable herbicidal activity is stably exhibited. A solid herbicidal composition comprising (1) 1-(4,6-dimethoxypyrimidin-2-yl)-3-(3-trifluoromethyl-2-pyridylsulfonyl)urea or its salt and (2) at least one surfactant selected from the group consisting of a naphthalene sulfonate condensed with formaldehyde, an alkylnaphthalene sulfonate condensed with formaldehyde, a dialkylnaphthalene sulfonate condensed with formaldehyde and a polycarboxylate.

5 Claims, No Drawings

SOLID HERBICIDAL COMPOSITION

TECHNICAL FIELD

The present invention relates to a solid herbicidal composition in which decomposition of 1-(4,6-dimethoxypyrimidin-2-yl)-3-(3-trifluoromethyl-2-pyridylsulfonyl)urea (common name: flazasulfuron, hereinafter referred to as compound A) is suppressed.

BACKGROUND ART

A herbicide containing the compound A as an active ingredient is utilized in various applications since it can control various undesired weeds with a low dose. However, the compound A in the herbicide may decompose in some cases depending upon the conditions, and accordingly no desired herbicidal effects can be sufficiently achieved in some cases. Thus, various studies have been conducted on a method for suppressing decomposition of the compound A.

JP-A-9-143015 discloses a method for suppressing decomposition of the compound A in a granular herbicidal composition by using a dialkylsulfosuccinate or a benzoate. JP-A-2002-12509 discloses a method for suppressing decomposition of the compound A in a solid herbicidal composition by using a stabilizer such as boric anhydride, metaboric acid, quick lime, barium oxide, zeolite, calcium silicate, magnesium oxide or magnesium sulfate. JP-A-5-271021 discloses a method for suppressing decomposition of the compound A in a spray liquid having a herbicidal composition diluted with water by using inorganic magnesium salts.

However, these documents failed to disclose a method for suppressing decomposition of the compound A in a solid herbicidal composition by using a specific surfactant described hereinafter.

DISCLOSURE OF THE INVENTION

Problem that the Invention is to Solve

To suppress decomposition of the compound A, various methods have been attempted, but a more excellent method is strongly desired in view of practicability. Further, in a case where the compound A and 2-ethylamino-4-isopropylamino-6-methylthio-1,3,5-triazine (common name: ametryn, hereinafter referred to as compound B) are blended to prepare a solid herbicidal composition, not only suppression of decomposition of the compound A but also disintegrability of the solid herbicidal composition in water has to be improved.

Means to Solve the Problem

The present inventors have conducted extensive studies to solve the above problem and as a result, they have found that decomposition of the compound A or its salt in a solid herbicidal composition can be suppressed by using a specific surfactant. Further, they have also found that when the compound A and the compound B are blended to prepare a solid herbicidal composition, not only suppression of decomposition of the compound A but also disintegrability of the solid herbicidal composition in water can be improved.

Namely, the present invention relates to a solid herbicidal composition comprising (1) the compound A or its salt and (2) at least one surfactant selected from the group consisting of a naphthalene sulfonate condensed with formaldehyde, an alkylnaphthalene sulfonate condensed with formaldehyde, a dialkylnaphthalene sulfonate condensed with formaldehyde and a polycarboxylate.

According to the present invention, a solid herbicidal composition with which the herbicidal activity of the compound A or its salt can be stably exhibited, is provided.

BEST MODE FOR CARRYING OUT THE INVENTION

Examples of the salt of the compound A used in the present invention include various ones, such as salts of alkali metals such as sodium and potassium, salts of alkaline earth metals such as magnesium and calcium, and salts of amines such as monomethylamine, dimethylamine and triethylamine.

Examples of the salt moiety in the naphthalene sulfonate condensed with formaldehyde, the alkylnaphthalene sulfonate condensed with formaldehyde and the dialkylnaphthalene sulfonate condensed with formaldehyde used in the present invention include various ones such as salts of alkali metals such as sodium and potassium, and salts of alkaline earth metals such as magnesium and calcium.

The alkyl moiety in the alkylnaphthalene sulfonate condensed with formaldehyde or the dialkylnaphthalene sulfonate condensed with formaldehyde used in the present invention may be linear or branched, and examples thereof include $C_{1-12}$ alkyls such as methyl, ethyl, propyl, butyl, pentyl, hexyl, heptyl, octyl, nonyl, decyl, undecyl and dodecyl.

Examples of the polycarboxylic acid moiety in the polycarboxylate used in the present invention include polyacrylic acid, polymethacrylic acid, a copolymer of acrylic acid/maleic acid and a copolymer of acrylic acid/sulfonic acid. Examples of the salt moiety in the polycarboxylate include various ones, such as salts of alkali metals such as sodium and potassium, and salts of alkaline earth metals such as magnesium and calcium.

The solid herbicidal composition of the present invention comprises (1) a compound A or its salt and (2) at least one surfactant (hereinafter referred to as an essential surfactant) selected from the group consisting of a naphthalene sulfonate condensed with formaldehyde, an alkylnaphthalene sulfonate condensed with formaldehyde, a dialkylnaphthalene sulfonate condensed with formaldehyde and a polycarboxylate, and is prepared as a solid herbicidal composition in the form of e.g. dusts, wettable powders, water dispersible granules, granules, water soluble powders, water soluble granules, water soluble packs, tablets, emulsifiable granules or emulsifiable powders. When such a composition is prepared, various additives may be used if desired. The additives may be any additives so long as they are commonly used in this technical field, and examples thereof include another surfactant (surfactant other than the essential surfactant), a carrier, a binder, an oil is absorbent, an antidrifting agent, a bubble agent, a drying agent and a solvent. The following may be mentioned as specific examples of such additives. These formulations may be prepared in accordance with a conventional method in this technical field.

Another surfactant may, for example, be an anionic surfactant such as a salt of fatty acid, a benzoate, an alkylsulfosuccinate, a dialkylsulfosuccinate, a salt of alkylsulfuric acid ester, an alkyl sulfate, an alkyl diglycol ether sulfate, a salt of alcohol sulfuric acid ester, an alkyl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether-sulfate, a polyoxyethylene styrylaryl ether sulfate, an ammonium salt of polyoxyethylene styrylaryl ether sulfuric acid, a salt of polyoxyethylene alkylaryl ether sulfuric acid ester, a polyoxyethylene alkyl ether phosphate, a salt of polyoxyethylene alkylaryl phosphoric acid ester, a polyoxyethylene styrylaryl ether phosphoric acid ester or its salt; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene hydrogenated castor oil, a polyoxyethylene castor oil or a polyoxypropylene fatty acid ester; or a cationic surfactant such as an alkoxylated fatty amine. A mixture of two or more of them may be used if desired.

The carrier may, for example, be diatomaceous earth, slaked lime, calcium carbonate, talc, white carbon, bentonite, starch, a saccharide such as lactose or fructose, sodium carbonate, sodium bicarbonate, clay, zeolite, ammonium sulfate, ammonium hydrogensulfate, sodium sulfate, sodium chloride or potassium chloride. A mixture of two or more of them may be used if desired.

Examples of the binders include various gums such as cyamoposis gum, locust bean gum, tragacanth gum, xanthan gum, and gum arabic; alginic acid derivatives such as sodium alginate, ammonium alginate, and propylene glycol alginate; organic polymer compounds such as polyvinyl alcohol, polyvinyl pyrrolidone, polyvinyl methacrylate, polyethylene oxide, polyacrylic acid, sodium polyacrylate and polyacrylamide; animal or vegetable water-soluble proteins such as albumen, albumin, casein, and gelatin; cellulose derivatives such as methylcellulose, caboxymethylcellulose, sodium salt of carboxymethylcellulose, carboxyethylcellulose, hydroxyethylcellulose, hydroxypropylcellulose, and hydroxypropylmethylcellulose; starches such as dextrin, starch, sodium salt of carboxymethylstarch, hydroxyethylstarch, and hydroxypropylstarch; and ligninsulfonic acid derivatives such as sodium lignihsulfonate, and calcium ligninsulfonate. A mixture of two or more of them may be used if desired.

The material of a water soluble film to be used for a water soluble pack may, for example, be polyvinyl alcohol or polyethylene glycol.

In the present invention, if desired, another herbicidal compound other than the compound A or its salt may be used in combination, whereby more excellent effects or synergistic effects may be presented in some cases. For example, the range of weeds to be controlled, the time of application of the composition, the herbicidal activities, etc., may be improved to preferred directions.

Another herbicidal compound to be used in combination with the compound A or its salt may, for example, be the above compound B, and in addition, the following group of compounds (1) to (11) (common names, developing codes) may be mentioned. Even when not specifically mentioned here, in a case where such compounds have salts, alkylesters, optical isomers, etc., they are, of course, all included. One type or more of the compound B or the following compound group may suitably be used in combination with the compound A or its salt.

(1) Those which are believed to exhibit herbicidal effects by disturbing hormone activities of plants, such as a phenoxy type such as 2,4-D, 2,4-DB, 2,4-DP, MCPA, MCPB, MCPP, naproanilide or clomeprop, an aromatic carboxylic acid type such as 2,3,6-TBA, dicamba, dichlobenil, picloram, triclopyr, clopyralid or aminopyralid, and others such as naptalam, benazolin, quinclorac, quinmerac, diflufenzopyr and thiazopyr.

(2) Those which are believed to exhibit herbicidal effects by inhibiting photosynthesis of plants, such as a urea type such as chlorotoluron, diuron, fluometuron, linuron, isoproturon, metobenzuron or tebuthiuron, a triazine type such as simazine, atrazine, atratone, simetryn, prometryn, dimethametryn, hexazinone, metribuzin, terbuthylazine, cyanazine, cybutryne, triaziflam or propazine, a uracil type such as bromacil, lenacil or terbacil, an anilide type such as propanil or cypromid, a carbamate type such as swep, desmedipham or phenmedipham, a hydroxybenzonitrile type such as bromoxynil, bromoxynil-octanoate or ioxynil, and others such as pyridate, bentazone, amicarbazone and methazole.

(3) Quaternary ammonium salt type such as paraquat or diquat, which is believed to be converted to free radicals by itself to form active oxygen in the plant body.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen-sodium, fomesafen, oxyfluorfen, lactofen or ethoxyfen-ethyl, a cyclic imide type such as chlorphthalim, flumioxazin, flumiclorac-pentyl or fluthiacet-methyl, and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, metobenzuron, cinidon-ethyl, flupoxam, fluazolate, profluazol, pyrachlonil, flufenpyr-ethyl and bencarbazone.

(5) Those which are believed to exhibit herbicidal effects characterized by bleaching activities by inhibiting chromogenesis of plants such as carotenoids, such as a pyridazinone type such as norflurazon, chloridazon or metflurazon, a pyrazole type such as pyrazolate, pyrazoxyfen, benzofenap, topramezone (BAS-670H) or pyrasulfotole, and others such as amitrol, fluridone, flurtamone, diflufenican, methoxyphenone, clomazone, sulcotrione, mesotrione, tembotrione, tefuryltrione (AVH-301), isoxaflutole, difenzoquat, isoxachlortole, benzobicyclon, picolinafen and beflubutamid.

(6) Those which exhibit strong herbicidal effects specifically to gramineous plants, such as an aryloxyphenoxypropionic acid type such as diclofop-methyl, flamprop-M-methyl, pyriphenop-sodium, fluazifop-butyl, haloxyfop-methyl, quizalofop-ethyl, cyhalofop-butyl, fenoxaprop-ethyl or metamifop-propyl, and a cyclohexanedione type such as alloxydim-sodium, clethodim, sethoxydim, tralkoxydim, butroxydim, tepraloxydim, caloxydim, clefoxydim or profoxydim.

(7) Those which are believed to exhibit herbicidal effects by inhibiting an amino acid biosynthesis of plants, such as a sulfonylurea type such as chlorimuron-ethyl, sulfometuron-methyl, primisulfuron-methyl, bensulfuron-methyl, chlorsulfuron, metsulfuron-methyl, cinosulfuron, pyrazosulfuron-ethyl, azimsulfuron, rimsulfuron, nicosulfuron, imazosulfuron, cyclosulfamuron, prosulfuron, flupyrsulfuron, triflusulfuron-methyl, halosulfuron-methyl, thifensulfuron-methyl, ethoxysulfuron, oxasulfuron, ethametsulfuron, iodosulfuron, sulfosulfuron, triasulfuron, tribenuron-methyl, tritosulfuron, foramsulfuron, trifloxysulfuron, mesosulfuron-methyl, orthosulfamuron, flucetosulfuron, amidosulfuron, TH-547, or a compound disclosed in WO2005092104, a triazolopyrimidinesulfonamide type such as flumetsulam, metosulam, diclosulam, cloransulam-methyl, florasulam, is metosulfam or penoxsulam, an imidazolinone type such as imazapyr, imazethapyr, imazaquin, imazamox, imazameth, imazamethabenz or imazapic, a pyrimidinylsalicylic acid type such as pyrithiobac-sodium, bispyribac-sodium, pyriminobac-methyl, pyribenzoxim, pyriftalid or pyrimisulfan (KUH-021), a sulfonylaminocarbonyltriazolinone type such as flucarbazone or procarbazone-sodium, and others such as glyphosate, glyphosate-sodium, glyphosate-potassium, glyphosate-ammonium, glyphosate-isopropylamine, sulfosate, glufosinate, glufosinate-ammonium and bilanafos.

(8) Those which are believed to exhibit herbicidal effects by inhibiting cell mitoses of plants, such as a dinitroaniline type such as trifluralin, oryzalin, nitralin, pendimethalin, ethalfluralin, benfluralin or prodiamine, an amide type such as bensulide, napronamide or pronamide, an organic phosphorus type such as amiprofos-methyl, butamifos, anilofos or piperophos, a phenylcarbamate type such as propham, chlorpropham or barban, a cumylamine type such as daimuron, cumyluron or bromobutide, and others such as asulam, dithiopyr and thiazopyr.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachloror propisochlor, a carbamate type such as molinate, dimepiperate or pyributicarb, and others such as etobenzanid, mefenacet, flufenacet, tridiphane, cafenstrole, fentrazamide, oxaziclomefone, indanofan, dimethenamid, benfuresate and pyroxasulfone (KIH-485).

(10) A thiocarbamate type such as EPTC, butylate, vernolate, pebulate, cycloate, prosulfocarb, esprocarb, thiobencarb, diallate or triallate, and others such as MSMA, DSMA, endothall, ethofumesate, sodium chlorate, pelargonic acid, fosamine, pinoxaden and HOK-201.

(11) Those which are believed to exhibit herbicidal effects by being parasitic on plants, such as *Xanthomonas campestris, Epicoccosurus nematosurus, Exserohilum monoseras* and *Drechsrela monoceras.*

The mix ratio of the respective components in the solid herbicidal composition of the present invention cannot generally be defined, as it varies depending upon the type of components blended, the type of the formulation, the application conditions, etc. However, for example, the amount of the compound A or its salt is from 0.1 to 90 parts by weight, preferably from 1 to 30 parts by weight, and the amount of the essential surfactant is from 1 to 40 parts by weight, preferably from 1 to 30 parts by weight.

In a case where another surfactant is blended if desired, its amount is from 1 to 20 parts by weight, preferably from 1 to 10 parts by weight, and the amount of a carrier if blended is from 1 to 95 parts by weight, preferably from 1 to 80 parts by weight, the amount of a binder if blended is from 0.1 to 10 parts by weight, preferably from 0.1 to 5 parts by weight, and the amount of the another herbicidal compound such as the compound B if blended is from 2 to 95 parts by weight, preferably from 15 to 80 parts by weight.

The solid herbicidal composition of the present invention is capable of controlling a wide range of weeds or inhibiting their growth, by applying it to undesired plants or to a place where they grow, by e.g. foliar application, soil application or irrigation. The weeds include sedges (or Cyperaceae) such as *Cyperus brevifolius* (Rottb.) Hassk. and purple nutsedge (*Cyperus rotundus* L.), grasses (or gramineae) such as barnyardgrass (*Echinochloa crus-galli* L.), crabgrass (*Digitaria sanguinalis* L.), greenfoxtail (*Setaria viridis* L.), goosegrass (*Eleusine indica* L.), wild oat (*Avena fatua* L.), johnsongrass (*Sorghum halepense* L.) and quackgrass (*Agropyron repens* L.), and broad leaves such as velvetleaf (*Abutilon theophrasti* MEDIC.), tall morningglory (*Ipomoea purpurea* L.), common lambsquarters (*Chenopodium album* L.), prickly *sida* (*Sida spinosa* L.), common purslane (*Portulaca oleracea* L.), redroot pigweed (*Amaranthus retroflexus* L.), sicklepod (*Cassia obtusifolia* L.), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis* L.). The application range extends to agricultural fields such as crop plant fields, orchards and mulberry fields and non-agricultural fields such as forest land, farm roads, playgrounds, factory sites and lawn.

Now, the present invention will be described in further detail with reference to Examples. However, the present invention is by no means restricted thereto.

EXAMPLE 1

| | | |
|---|---|---|
| (1) | Compound A (purity 94.5%) | 21.16 parts by weight |
| (2) | Naphthalene sulfonate condensed with formaldehyde (tradename: Tamol NN8906, manufactured by BASF Japan Ltd.) | 10.00 parts by weight |
| (3) | Clay | 68.84 parts by weight |

The above respective components were mixed, and water was added to the mixture and kneaded. The kneaded product was granulated by an extruding granulator, dried and sieved to obtain water dispersible granules.

EXAMPLE 2

| | | |
|---|---|---|
| (1) | Compound A (purity 94.5%) | 1.06 parts by weight |
| (2) | Polycarboxylate (tradename: Geropon T/36, manufactured by Rhodia Nicca, Ltd.) | 10.00 parts by weight |
| (3) | Clay | 88.94 parts by weight |

The above respective components were mixed, and water dispersible granules were obtained in accordance with the above Example 1.

EXAMPLE 3

| | | |
|---|---|---|
| (1) | Compound A (purity 94.5%) | 5.29 parts by weight |
| (2) | Tamol NN8906 (as defined above) | 10.00 parts by weight |
| (3) | Geropon T/36 (as defined above) | 3.00 parts by weight |
| (4) | Clay | 81.71 parts by weight |

The above respective components were mixed, and water dispersible granules were obtained in accordance with the above. Example 1.

EXAMPLE 4

| | | |
|---|---|---|
| (1) | Compound A (purity 94.5%) | 2.65 parts by weight |
| (2) | Compound B (purity 95.5%) | 75.92 parts by weight |

-continued

| | | |
|---|---|---|
| (3) | Tamol NN8906 (as defined above) | 15.00 parts by weight |
| (4) | Geropon T/36 (as defined above) | 6.43 parts by weight |

The above respective components were mixed, and water dispersible granules were obtained in accordance with the above Example 1.

EXAMPLE 5

| | | |
|---|---|---|
| (1) | Compound A (purity 94.5%) | 2.65 parts by weight |
| (2) | Compound B (purity 95.5%) | 75.92 parts by weight |
| (3) | Tamol NN8906 (as defined above) | 5.00 parts by weight |
| (4) | Geropon T/36 (as defined above) | 16.43 parts by weight |

The above respective components were mixed, and water dispersible granules were obtained in accordance with the above Example 1.

EXAMPLE 6

| | | |
|---|---|---|
| (1) | Compound A (purity 94.8%) | 2.64 parts by weight |
| (2) | Compound B (purity 98.4%) | 67.75 parts by weight |
| (3) | Alkylnaphthalene sulfonate condensed with formaldehyde (tradename: Morwet D425, manufactured by LION AKZO CO., LTD.) | 10.00 parts by weight |
| (4) | Geropon T/36 (as defined above) | 3.00 parts by weight |
| (5) | Clay | 16.61 parts by weight |

The above respective components were mixed, and water dispersible granules were obtained in accordance with the above Example 1.

EXAMPLE 7

| | | |
|---|---|---|
| (1) | Compound A (purity 94.5%) | 2.65 parts by weight |
| (2) | Compound B (purity 95.5%) | 75.92 parts by weight |
| (3) | Tamol NN8906 (as defined above) | 10.00 parts by weight |
| (4) | Clay | 11.43 parts by weight |

The above respective components were mixed, and water dispersible granules were obtained in accordance with the above Example 1.

EXAMPLE 8

| | | |
|---|---|---|
| (1) | Compound A (purity 94.5%) | 2.65 parts by weight |
| (2) | Compound B (purity 95.5%) | 75.92 parts by weight |
| (3) | Tamol NN8906 (as defined above) | 10.00 parts by weight |
| (4) | Geropon T/36 (as defined above) | 3.00 parts by weight |
| (5) | Clay | 8.43 parts by weight |

The above respective components were mixed, and water dispersible granules were obtained in accordance with the above Example 1.

EXAMPLE 9

| | | |
|---|---|---|
| (1) | Compound A (purity 94.8%) | 2.64 parts by weight |
| (2) | Compound B (purity 98.4%) | 67.75 parts by weight |
| (3) | Alkylnaphthalene sulfonate condensed with formaldehyde (tradename: Supragil MNS/25, manufactured by Rhodia Nicca, Ltd.) | 10.00 parts by weight |
| (4) | Geropon T/36 (as defined above) | 3.00 parts by weight |
| (5) | Clay | 16.61 parts by weight |

The above respective components were mixed, and water dispersible granules were obtained in accordance with the above Example 1.

EXAMPLE 10

| | | |
|---|---|---|
| (1) | Compound A (purity 94.5%) | 2.65 parts by weight |
| (2) | Compound B (purity 96.5%) | 75.13 parts by weight |
| (3) | Alkylnaphthalene sulfonate condensed with formaldehyde (tradename: DEMOL SN-B, manufactured by Kao Corporation) | 10.00 parts by weight |
| (4) | Geropon T/36 (as defined above) | 3.00 parts by weight |
| (5) | Clay | 9.22 parts by weight |

The above respective components were mixed, and water dispersible granules were obtained in accordance with the above Example 1.

EXAMPLE 11

| | | |
|---|---|---|
| (1) | Compound A (purity 94.5%) | 2.65 parts by weight |
| (2) | Compound B (purity 96.5%) | 75.13 parts by weight |
| (3) | Naphthalene sulfonate condensed with formaldehyde (tradename: DEMOL N, manufactured by Kao Corporation) | 10.00 parts by weight |
| (4) | Geropon T/36 (as defined above) | 3.00 parts by weight |
| (5) | Clay | 9.22 parts by weight |

The above respective components were mixed, and water dispersible granules were obtained in accordance with the above Example 1.

COMPARATIVE EXAMPLE 1

| | | |
|---|---|---|
| (1) | Compound A (purity 94.5%) | 2.65 parts by weight |
| (2) | Compound B (purity 95.5%) | 75.92 parts by weight |
| (3) | Alkylnaphthalene sulfonate (tradename: NK BX-C, manufactured by TAKEMOTO OIL & FAT Co., Ltd.) | 10.00 parts by weight |
| (4) | Clay | 11.43 parts by weight |

The above respective components were mixed, and water dispersible granules were obtained in accordance with the above Example 1.

TEST EXAMPLE 1

The water dispersible granules obtained in Examples 1 to 5 were stored in a thermostatic oven at 54° C. for 14 days. The content of the compound A in the water dispersible granules before and after the storage was quantitatively determined by liquid chromatography, and the decomposition rate of each water dispersible granules was calculated from the following formula to evaluate the change with time. The results are shown in Table 1.

$$\text{Decomposition rate } (\%) = \{(X-Y)/X\} \times 100$$

X: content immediately after preparation
Y: content after storage

TABLE 1

| Examples | Decomposition rate of compound A (%) |
|---|---|
| 1 | 1.1 |
| 2 | 3.9 |
| 3 | 2.1 |
| 4 | 0.4 |
| 5 | 0.9 |

TEST EXAMPLE 2

100 ml of CIPAC standard water D (342 ppm hardness) was put in a test tube with glass-stopper (inner diameter 23 mm, height 225 mm). 0.5 g of the water dispersible granules after subjected to evaluation of the change with time in the above Test Example 1 was added to the test tube, and one minute later, the test tube was plugged and inverted, and the inverted times until the water dispersible granules were completely disintegrated were counted. The results are shown in Table 2.

TABLE 2

| Examples | Inverted times |
|---|---|
| 1 | 15 |
| 2 | 15 |
| 3 | 10 |
| 4 | 7 |
| 5 | 12 |

TEST EXAMPLE 3

In the same manner as in Test Example 1, the changes with time of the water dispersible granules obtained in Examples 6 to 8 were evaluated. The results are shown in Table 3.

TABLE 3

| Examples | Decomposition rate of compound A (%) |
|---|---|
| 6 | 0.6 |
| 7 | 3.1 |
| 8 | 0.9 |

TEST EXAMPLE 4

In the same manner as in Test Example 1, the changes with time of the water dispersible granules obtained in Examples 9 to 11 were evaluated. The results are shown in Table 4.

TABLE 4

| Examples | Decomposition rate of compound A (%) |
|---|---|
| 9 | 1.3 |
| 10 | 3.3 |
| 11 | 2.0 |

TEST EXAMPLE 5

In the same manner as in Test Example 2, the inverted times until the water dispersible granules obtained in the above Examples 9 to 11 were completely disintegrated were counted. The results are shown in Table 5.

TABLE 5

| Examples | Inverted times |
|---|---|
| 9 | 12 |
| 10 | 5 |
| 11 | 8 |

COMPARATIVE TEST EXAMPLE

In the same manner as in Test Example 1, the change with time of the water dispersible granules obtained in Comparative Example 1 was evaluated, whereupon the decomposition rate of the compound A was 45.2%. Further, in the same manner as in Test Example 2, the inverted times until the water dispersible granules were completely disintegrated were counted, whereupon they were not completely disintegrated even after inversion 100 times.

The invention claimed is:

1. A solid herbicidal composition comprising (1) 1-(4,6-dimethoxypyrimidin-2-yl)-3-(3-trifluoromethyl-2-pyridylsulfonyl)urea or its salt and (2) at least one surfactant selected from the group consisting of (a) a naphthalene sulfonate condensed with formaldehyde and a polycarboxylate and (b) an alkylnaphthalene sulfonate condensed with formaldehyde and a polycarboxylate, with the proviso that the solid herbicidal composition does not comprise a dialkylsulfosuccinate and the solid herbicidal composition does not comprise an alkoxylated glyceride, wherein said solid herbicidal composition is in the form of water dispersible granules.

2. The solid herbicidal composition according to claim 1, which further comprises a carrier.

3. The solid herbicidal composition according to claim 1, which further comprises another herbicidal compound.

4. The solid herbicidal composition according to claim 3, wherein the another herbicidal compound is 2-ethylamino-4-isopropylamino-6-methylthio-1,3,5-triazine.

5. A method for stabilizing 1-(4,6-dimethoxypyrimidin-2-yl)-3-(3-trifluoromethyl-2-pyridylsulfonyl)urea or its salt in the solid herbicidal water dispersible granules according to claim 1, said method comprising mixing said 1-(4,6-dimethoxypyrimidin-2-yl)-3-(3-trifluoromethyl-2-pyridylsulfonyl)urea or said salt with at least one surfactant selected from the group consisting of (a) a naphthalene sulfonate condensed with formaldehyde and a polycarboxylate and (b)

an alkylnaphthalene sulfonate condensed with formaldehyde and a polycarboxylate, with the proviso that neither a dialkylsulfosuccinate nor an alkoxylated glyceride are added to the mixture.

* * * * *